United States Patent
Wysopal et al.

(10) Patent No.: US 12,208,037 B2
(45) Date of Patent: *Jan. 28, 2025

(54) MONITORING LASER PULSE ENERGY IN A LASER EYE SURGERY SYSTEM

(71) Applicant: AMO DEVELOPMENT, LLC, Irvine, CA (US)

(72) Inventors: Jan C. Wysopal, Livermore, CA (US); Yu-Tai Ray Chen, Union City, CA (US)

(73) Assignee: AMO Development, LLC, Irvine, CA (US)

( * ) Notice: Subject to any disclaimer, the term of this patent is extended or adjusted under 35 U.S.C. 154(b) by 70 days.

This patent is subject to a terminal disclaimer.

(21) Appl. No.: 18/161,007

(22) Filed: Jan. 27, 2023

(65) Prior Publication Data

US 2023/0172755 A1 Jun. 8, 2023

Related U.S. Application Data

(60) Continuation of application No. 16/852,354, filed on Apr. 17, 2020, now Pat. No. 11,564,837, which is a division of application No. 14/069,137, filed on Oct. 31, 2013, now Pat. No. 10,624,786.

(60) Provisional application No. 61/721,669, filed on Nov. 2, 2012.

(51) Int. Cl.
 A61F 9/008 (2006.01)
(52) U.S. Cl.
 CPC .............. *A61F 9/00825* (2013.01); *A61F 2009/00844* (2013.01); *A61F 2009/00846* (2013.01); *A61F 2009/0087* (2013.01); *A61F 2009/00872* (2013.01); *A61F 2009/00887* (2013.01)

(58) Field of Classification Search
 CPC ........ A61F 9/00825; A61F 2009/00844; A61F 2009/00846; A61F 2009/0087; A61F 2009/00872; A61F 2009/00887
 USPC ........................................................... 606/5
 See application file for complete search history.

(56) References Cited

U.S. PATENT DOCUMENTS

| | | |
|---|---|---|
| 5,275,594 A | 1/1994 | Baker et al. |
| 5,459,570 A | 10/1995 | Swanson et al. |
| 5,720,894 A | 2/1998 | Neev et al. |
| 5,748,352 A | 5/1998 | Hattori |
| 5,748,898 A | 5/1998 | Ueda |
| 5,957,915 A | 9/1999 | Trost |
| 5,984,916 A | 11/1999 | Lai |
| 6,019,472 A | 2/2000 | Koester et al. |
| 6,053,613 A | 4/2000 | Wei et al. |

(Continued)

*Primary Examiner* — Aaron F Roane

(57) ABSTRACT

A photo detector is selectively coupled to a first integrator or a second integrator with switching circuitry when the laser pulses. An integration time of the signal from the photo detector can be substantially greater than an amount of time between successive laser beam pulses in order to provide an accurate measurement of each laser beam pulse of a high repetition rate pulsed laser. The laser may comprise a clock coupled to an optical switch of the laser system, and control circuitry can control switching and coupling of the detector to the first integrator or the second integrator in response to the clock signal. The first integrator and the second integrator can be selectively coupled to an output such that the first integrator or the second integrator is coupled to the output of the energy detection circuitry when the other integrator is coupled to the detector.

23 Claims, 8 Drawing Sheets

(56) References Cited

U.S. PATENT DOCUMENTS

| | | | |
|---|---|---|---|
| 6,111,645 | A | 8/2000 | Tearney et al. |
| 6,454,761 | B1 | 9/2002 | Freedman |
| 7,655,002 | B2 | 2/2010 | Myers et al. |
| 7,717,907 | B2 | 5/2010 | Ruiz et al. |
| 8,262,646 | B2 | 9/2012 | Frey et al. |
| 8,350,183 | B2 | 1/2013 | Vogel et al. |
| 8,382,745 | B2 | 2/2013 | Naranjo-Tackman et al. |
| 8,414,564 | B2 | 4/2013 | Goldshleger et al. |
| 10,624,786 | B2 * | 4/2020 | Wysopal .............. A61F 9/00825 |
| 2003/0025971 | A1 | 2/2003 | Price et al. |
| 2011/0319873 | A1 | 12/2011 | Raksi et al. |
| 2011/0319875 | A1 | 12/2011 | Loesel et al. |

\* cited by examiner

300 ↘

305- Determine type of treatment, for example type of material, surgical procedure, location of treatment 310- Receive treatment input from user 315- Receive patient measurement data 320- Determine series of pulses to cut anterior lens capsule with 3D cutting of capsule 325- Determine series of pulses to fragment cortex and nucleus with 3D cutting 330- Select first detector or second detector to measure pulses (or both)

335- Measure energy of each pulse of a series of calibration pulses

340- Reset first integrator

345- Couple first integrator to detector

350- Transmit first laser beam pulse

355- Receive first pulse with photo detector

360- Start Integration of first pulse with first integrator

365- Reset second integrator

370- Decouple first integrator from detector

375- Couple first integrator to conditioning circuit with integrator output selector 380- Couple second integrator to detector 385- Transmit second laser beam pulse 390- Receive second laser pulse with photo detector 395- Start Integration of second pulse with second integrator 400- Complete integration of first pulse 405- Transmit amount of energy of first pulse to system controller 410- Reset first integrator 415- Couple first integrator to detector 420- Decouple second integrator from integrator 425- Couple second integrator to conditioning circuitry with integrator output 430- Complete integration of second pulse 435- Transmit amount of energy of second pulse to system controller 440- Repeat above steps to measure energy of each pulse of the laser calibration 445- Adjust output 450- Treat patient 455- Measure each pulse of series of pulses of patient treatment 460- Adjust output during treatment 465- Complete treatment

FIG. 8

MONITORING LASER PULSE ENERGY IN A LASER EYE SURGERY SYSTEM

CROSS-REFERENCE TO RELATED APPLICATIONS

This application is a continuation and claims priority to U.S. patent application Ser. No. 16/852,354, filed Apr. 17, 2020, which is a divisional of and claims priority to U.S. patent application Ser. No. 14/069,137, filed Oct. 31, 2013, issued as U.S. patent Ser. No. 10/624,786 on Apr. 21, 2020, which claims the benefit of priority to U.S. Provisional Application No. 61/721,669, filed Nov. 2, 2012. The contents of the above applications are incorporated herein by reference in their entireties.

BACKGROUND

The present disclosure relates generally to energy monitoring of pulsed lasers to treat a material, such as a tissue of an eye. Although specific reference is made to cutting tissue for surgery such as eye surgery, embodiments as described herein can be used in many ways with many materials to treat one or more of many materials, such as cutting of optically transparent materials. Embodiments as described herein for improved laser energy monitoring can also be used for detector computed tomography, sample analysis instrument, laser light regulations, and many applications involving medical surgery.

Cutting of materials can be done mechanically with chisels, knives, scalpels and other tools such as surgical tools. However, prior methods and apparatus of cutting can be less than desirable and provide less than ideal results in at least some instances. For example, at least some prior methods and apparatus for cutting materials such as tissue may provide a somewhat rougher surface than would be ideal. Although lasers having pulse short pulse durations have been proposed to cut tissue, these short pulsed lasers may use very high pulse repetition rates and the energy of these lasers can be difficult to measure in at least some instances. Pulsed lasers can be used to cut one or more of many materials and have been used for laser surgery to cut tissue.

Examples of surgically tissue cutting include cutting the cornea and crystalline lens of the eye. The lens of the eye can be cut to correct a defect of the lens, for example to remove a cataract, and the tissues of the eye can be cut to access the lens. For example the cornea can be cut to access the cataractous lens. The cornea can be cut in order to correct a refractive error of the eye, for example with laser assisted in situ keratomileusis (hereinafter "LASIK").

Many patients may have visual errors associated with the refractive properties of the eye such as nearsightedness, farsightedness and astigmatism. Astigmatism may occur when the corneal curvature is unequal in two or more directions. Nearsightedness can occur when light focuses before the retina, and farsightedness can occur with light refracted to a focus behind the retina. There are numerous prior surgical approaches for reshaping the cornea, including laser assisted in situ keratomileusis, all laser LASIK, femto LASIK, corneaplasty, astigmatic keratotomy, corneal relaxing incision (hereinafter "CRI"), and Limbal Relaxing Incision (hereinafter "LRI"). Astigmatic Keratotomy, Corneal Relaxing Incision (CRI), and Limbal Relaxing Incision (LRI), corneal incisions are made in a well-defined manner and depth to allow the cornea to change shape to become more spherical.

Cataract extraction is a frequently performed surgical procedure. A cataract is formed by opacification of the crystalline lens of the eye. The cataract scatters light passing through the lens and may perceptibly degrade vision. A cataract can vary in degree from slight to complete opacity. Early in the development of an age-related cataract the power of the lens may increase, causing near-sightedness (myopia). Gradual yellowing and opacification of the lens may reduce the perception of blue colors as those shorter wavelengths are more strongly absorbed and scattered within the cataractous crystalline lens. Cataract formation may often progresses slowly resulting in progressive vision loss.

A cataract treatment may involve replacing the opaque crystalline lens with an artificial intraocular lens (IOL), and an estimated 15 million cataract surgeries per year are performed worldwide. Cataract surgery can be performed using a technique termed phacoemulsification in which an ultrasonic tip with associated irrigation and aspiration ports is used to sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by performing an anterior capsulotomy in which a small round hole can be formed in the anterior side of the lens capsule. Access to the lens nucleus can also be provided by performing a manual continuous curvilinear capsulorhexis (CCC) procedure. After removal of the lens nucleus, a synthetic foldable intraocular lens (IOL) can be inserted into the remaining lens capsule of the eye.

Prior short pulse laser systems have been used to cut tissue, and have been used to treat many patients. The short pulses have a temporal duration that is short enough to provide optical breakdown with plasma formation to cut tissue. These laser systems rely on very accurate placement of the pulses, and a patient interface may be employed to align the laser with tissue. However, the patient interface can be somewhat cumbersome for users and may result in increased intraocular pressure in at least some instances, and it would be helpful to provide treatments quickly with less reliance on the patient interface. Variability of the tissue location where optical breakdown occurs may result in tissue cutting that may be somewhat rougher than would be ideal in at least some instances. Laser cutting of the cataractous lens can result in the formation of gas bubbles that may interfere with the cutting of subsequent pulses, and treatments with less gas formation may result in more complete cutting of the lens tissue. The patient may move during treatment, which may result in incomplete or partial treatment of the tissue. Also, calibrating the energy of the laser used for treatment can be less accurate than would be ideal in at least some instances, for example energy calibration with high repetition rate short pulse lasers.

Thus, improved methods and systems would be helpful for treating materials with laser beams, such as the surgical cutting of tissue to treat cataracts and refractive errors of the eye.

SUMMARY

The improved methods and apparatus for energy detection as described herein can be used to measure the energy of pulsed lasers more accurately at fast laser pulse rates and can provide treatment of material with optical breakdown with increased accuracy and repeatability. In many embodiments, a laser system is used to control the location of optical break down within one or more materials, and information related to the energy of each pulse can be used to adjust the laser system to improve the treatment. The treated material may comprise a soft or hard material, and can be an inorganic or an organic material such as a tissue. The tissue may comprise a tissue of an eye such as one or more of corneal, lenticular, or retinal tissue. The energy detection methods and apparatus can measure energy accurately, so as to allow faster treatments with decreased reliance on the patient interface and provide smoother more uniform cuts with decreased gas formation.

The laser system may comprise a pulsed laser, a scanning module to position the laser beam optical breakdown in three dimensions, and energy detector circuitry to measure the energy of pulses of the laser beam. The amount of energy of each pulse of a series of pulses can be measured for a high pulse repetition rate pulsed laser beam, and the output energy or an optical component of the laser adjusted in response to the measured energy. The series of pulses may comprise a plurality of pulses having a first pulse and a second pulse. A photo detector can be selectively coupled to a first integrator or a second integrator with switching circuitry when the laser pulses, such that an integration time of the signal from the photo detector can be substantially greater than an amount of time between successive laser beam pulses. The integration times of the plurality of detectors that are greater than the time between successive laser beam pulses can substantially increase accuracy of the measurements of the beam pulses, and in many embodiments provides a measurement of each laser beam pulse of a high repetition rate pulse laser. The photo detector can be coupled to the first integrator to measure the first pulse and the second integrator to measure the second pulse. The laser may comprise one or more of a clock or synchronization signal coupled to an optical switch of the laser system, and control circuitry of the energy detector can control switching and coupling of the detector to the first integrator or the second integrator in response to the one or more of the clock signal or the synchronization signal. The first integrator and the second integrator can be selectively coupled to an output such that the first integrator or the second integrator is coupled to the output of the energy detection circuitry. In many embodiments, the first integrator is coupled to the photo detector when the second integrator is coupled to the output, and the second integrator is coupled to the energy detector when the first integrator is coupled to the output.

In a first aspect, embodiments provide an apparatus to treat a material with pulsed light energy. The apparatus comprises a pulsed laser to generate light energy comprising a plurality of pulses to treat the material, and a detector responsive to the light energy. A plurality of integrators comprising a first integrator and a second integrator is coupled to the detector. Switching circuitry is coupled to the pulsed laser, the detector and the plurality of integrators in order to couple the detector to the first integrator for a first pulse of the light energy and the second integrator for a second pulse of the light energy.

In another aspect, embodiments provide a method of treating a material with pulsed light energy. The method comprises pulsing a laser to generate light energy comprising a plurality of pulses to treat the material. A portion of the light energy is received with a detector responsive to the light energy. A plurality of integrators is selectively coupled to the detector. The detector comprises a first integrator and a second integrator. The detector is coupled to the first integrator for a first pulse of the light energy and coupled to the second integrator for a second pulse of the light energy.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIG. 8 shows a method of treating a material such as tissue, in accordance with many embodiments.

DETAILED DESCRIPTION

The embodiments as described herein can be used to treat one or more of many types of material such as hard materials, for example crystalline materials, or soft materials, for example tissue. The methods and apparatus as described herein can be particularly well suited for a treating a material at a penetration depth and may be combined in one or more of many ways, although the methods and apparatus as described herein can be used to treat a surface of a transparent or an opaque material, for example with photo ablation. The embodiments as describe herein are particularly well suited for treating tissue, such as with the surgical treatment of tissue. In many embodiments, the tissue comprises an optically transmissive tissue, such as tissue of an eye. The embodiments as described herein can be combined in many ways with one or more of many known surgical procedures such as cataract surgery, laser assisted in situ keratomileusis (hereinafter "LASIK"), laser assisted subepithelial keratectomy (hereinafter "LASEK").

Methods and systems related to laser treatment of materials and which can be used with eye surgery such as laser eye surgery are disclosed. A laser may be used to form precise incisions in the cornea, in the lens capsule, and/or in the crystalline lens nucleus, for example. The embodiments as described herein can be particularly well suited for adjusting the output energy amount of the laser beam, and can be used to adjust the optics of the laser beam, for example. In many embodiments, the laser system comprising the energy detector can be used to measure the energy of each pulse of the laser beam, and adjust the output energy of the laser beam based on the measured energy of each of the pulses. These measurements can be used with fast laser systems having a laser pulse repetition rate of at least about 50 kHz, for example at least about 100 kHz. Measuring the energy of each pulse and determining the variability of the laser beam output energy can be used in many beneficial ways to improve the treatment of the material such as a tissue of the eye.

System Configuration

Figure 1:
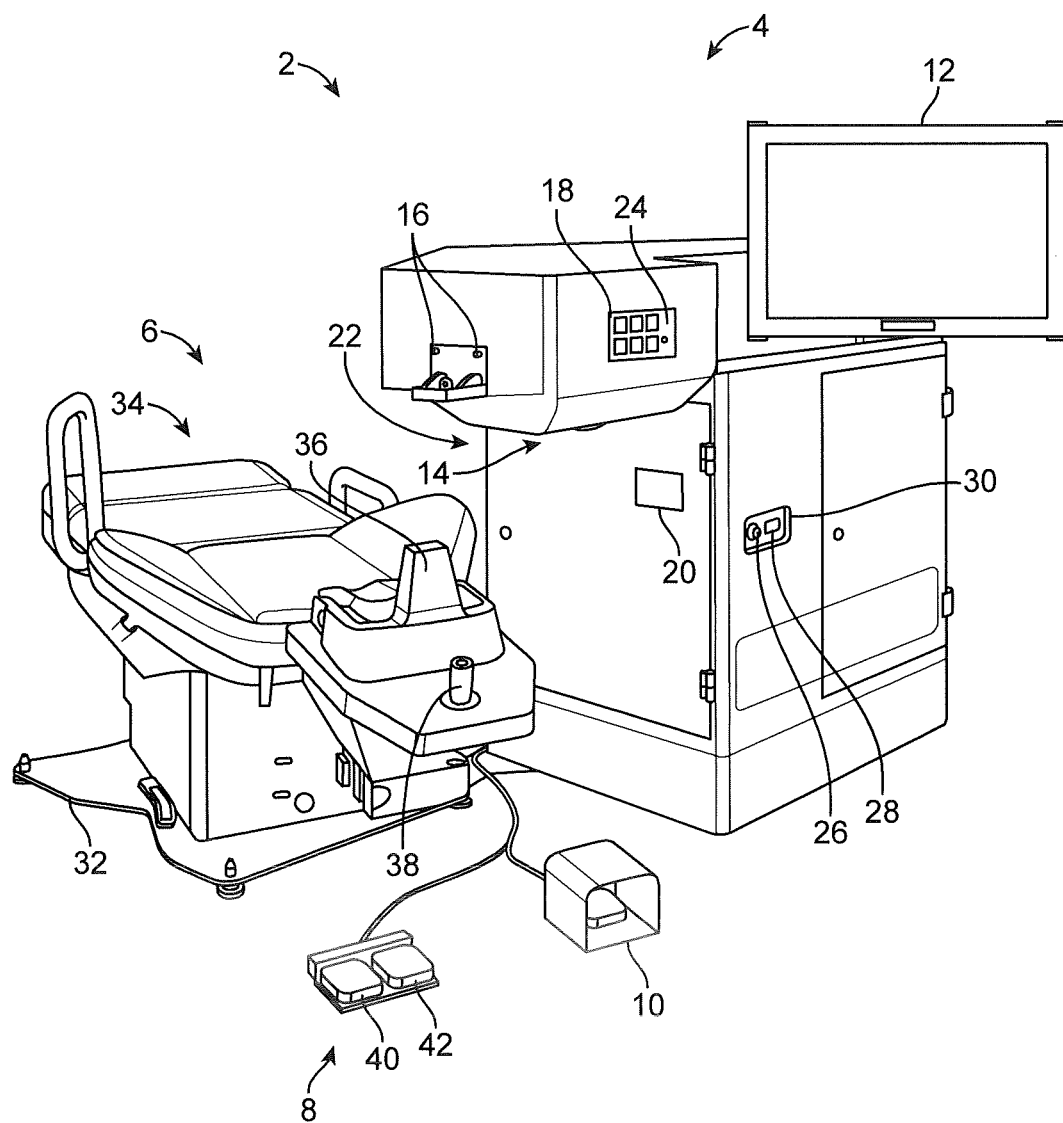
FIG. 1 is a perspective view showing a laser eye surgery system, in accordance with many embodiments.

FIG. 1 shows a laser eye surgery system 2, in accordance with many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38. To further protect against unintended chair motion, power supplied to the patient chair 6 may automatically be cut off using a switch.

In many embodiments, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user is without access to network based printing.

Figure 2:
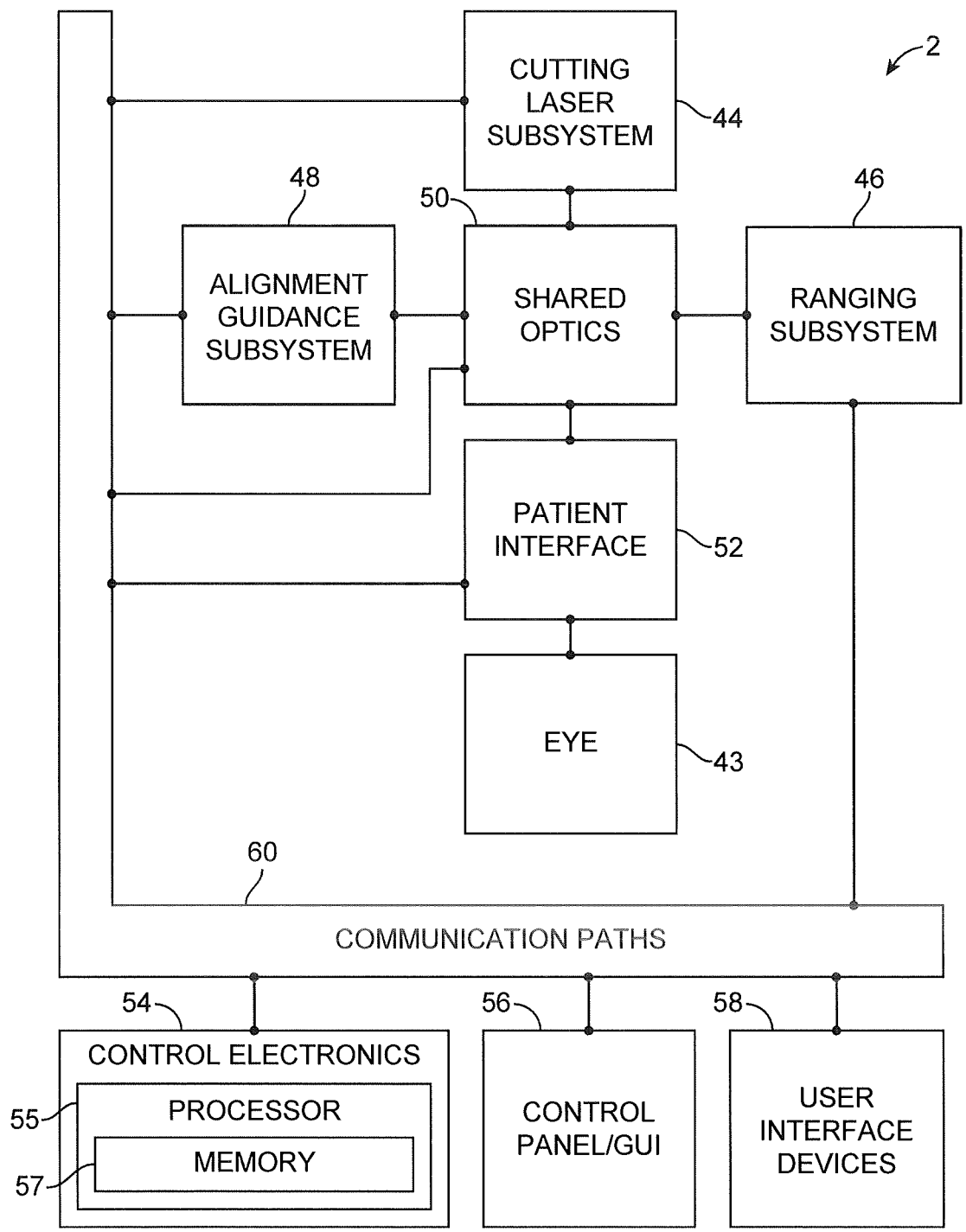
FIG. 2 is a simplified block diagram showing a top level view of the configuration of a laser eye surgery system, in accordance with many embodiments.

FIG. 2 shows a simplified block diagram of the system 2 coupled with a patient eye 43. The patient eye 43 comprises a cornea, a lens, and an iris. The iris defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

In many embodiments, the cutting laser subsystem 44 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes optical coherence tomography (OCT) imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, the ranging subsystem 46, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43. The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface and the patient's cornea and forms part of a transmission path between the shared optics 50 and the patient's eye 43. The optically transmissive structure may comprise a lens 96 having one or more curved surfaces. Alternatively, the patient interface 22 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components.

The control electronics 54 can include any suitable components, such as one or more processor, one or more field-programmable gate array (FPGA), and one or more memory storage devices. In many embodiments, the control electronics 54 controls the control panel/GUI 56 to provide for pre-procedure planning according to user specified treatment parameters as well as to provide user control over the laser eye surgery procedure.

The control electronics 54 may comprise a processor/controller 55 (referred to herein as a processor) that is used to perform calculations related to system operation and provide control signals to the various system elements. A computer readable medium 57 (also referred to as a database or a memory) is coupled to the processor 55 in order to store data used by the processor and other system elements. The processor 55 interacts with the other components of the system as described more fully throughout the present specification. In an embodiment, the memory 57 can include a look up table that can be utilized to control one or more components of the laser system as described herein.

The processor 55 can be a general purpose microprocessor configured to execute instructions and data, such as a Pentium processor manufactured by the Intel Corporation of Santa Clara, California. It can also be an Application Specific Integrated Circuit (ASIC) that embodies at least part of the instructions for performing the method in accordance with the embodiments of the present disclosure in software, firmware and/or hardware. As an example, such processors include dedicated circuitry, ASICs, combinatorial logic, other programmable processors, combinations thereof, and the like.

The memory 57 can be local or distributed as appropriate to the particular application. Memory 57 may include a number of memories including a main random access memory (RAM) for storage of instructions and data during program execution and a read only memory (ROM) in which fixed instructions are stored. Thus, memory 57 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 3:
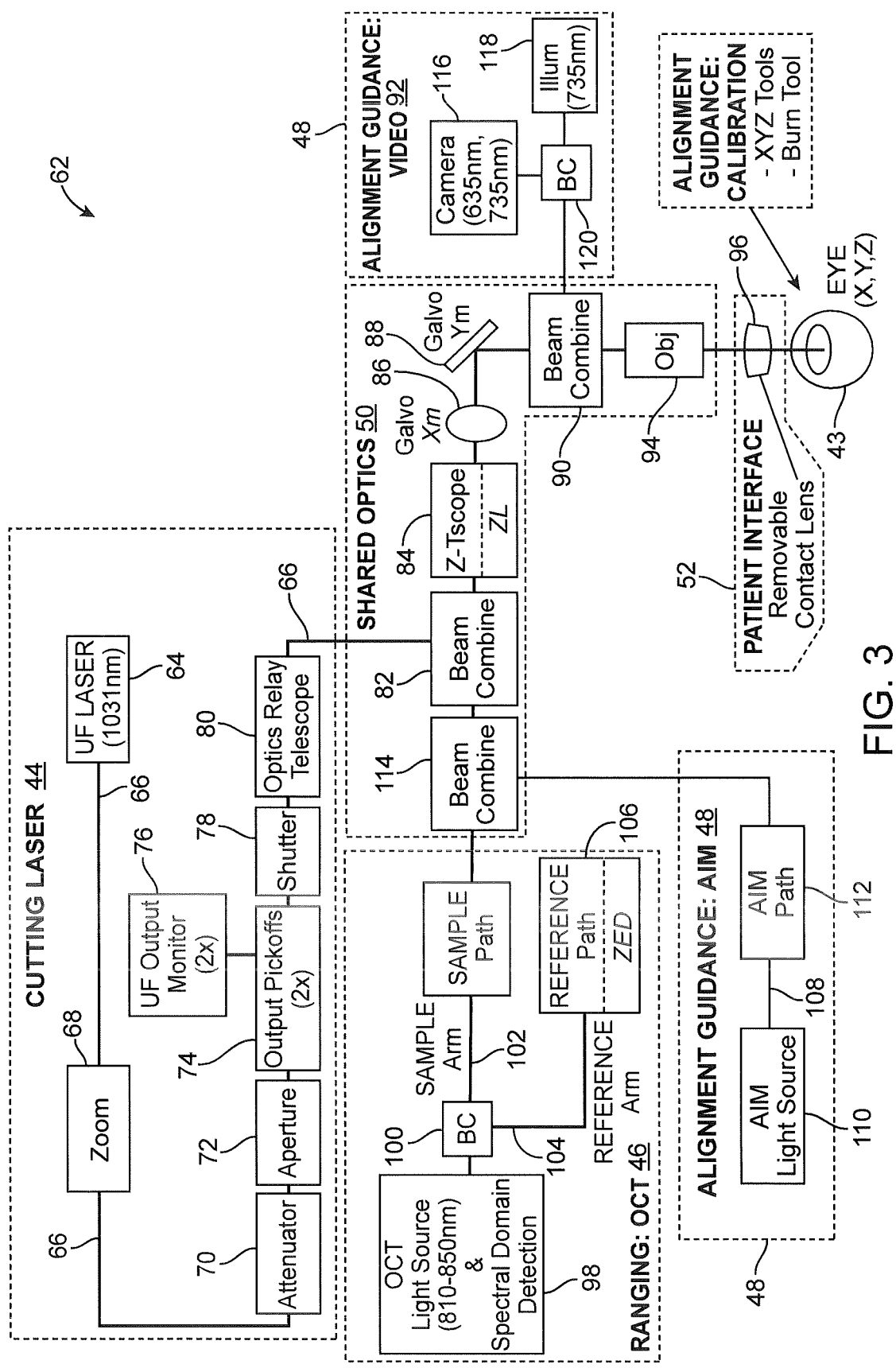
FIG. 3 is a simplified block diagram illustrating the configuration of an optical assembly of a laser eye surgery system, in accordance with many embodiments.

FIG. 3 is a simplified block diagram illustrating an assembly 62, in accordance with many embodiments, that can be included in the system 2. The assembly 62 is a non-limiting example of suitable configurations and integration of the cutting laser subsystem 44, the ranging subsystem 46, the alignment guidance subsystem 48, the shared optics 50, and the patient interface 52. Other configurations and integration of the cutting laser subsystem 44, the ranging subsystem 46, the alignment guidance subsystem 48, the shared optics 50, and the patient interface 52 may be possible and may be apparent to a person of skill in the art.

The assembly 62 is operable to project and scan optical beams into the patient's eye 43. The cutting laser subsystem 44 includes an ultrafast (UF) laser 64 (e.g., a femtosecond laser). Using the assembly 62, optical beams can be scanned in the patient's eye 43 in three dimensions: X, Y, Z. For example, short-pulsed laser light generated by the UF laser 64 can be focused into eye tissue to produce dielectric breakdown to cause photodisruption around the focal point (the focal zone), thereby rupturing the tissue in the vicinity of the photo-induced plasma. In the assembly 62, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43 and specifically within the crystalline lens and the lens capsule of the eye is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 64 can be a repetitively pulsed 1031 nm device that produces pulses with less than 600 fs duration at a repetition rate of 120 kHz (+/−5%) and individual pulse energy in the 1 to 20 micro joule range.

The cutting laser subsystem 44 is controlled by the control electronics 54 and the user, via the control panel/GUI 56 and the user interface devices 58, to create a laser pulse beam 66. The control panel/GUI 56 is used to set system operating parameters, process user input, display gathered information such as images of ocular structures, and display representations of incisions to be formed in the patient's eye 43.

The generated laser pulse beam 66 proceeds through a zoom assembly 68. The laser pulse beam 66 may vary from unit to unit, particularly when the UF laser 64 may be obtained from different laser manufacturers. For example, the beam diameter of the laser pulse beam 66 may vary from unit to unit (e.g., by +/−20%). The beam may also vary with regard to beam quality, beam divergence, beam spatial circularity, and astigmatism. In many embodiments, the zoom assembly 68 is adjustable such that the laser pulse beam 66 exiting the zoom assembly 68 has consistent beam diameter and divergence unit to unit.

After exiting the zoom assembly 68, the laser pulse beam 66 proceeds through an attenuator 70. The attenuator 70 is used to adjust the transmission of the laser beam and thereby the energy level of the laser pulses in the laser pulse beam 66. The attenuator 70 is controlled via the control electronics 54.

After exiting the attenuator 70, the laser pulse beam 66 proceeds through an aperture 72. The aperture 72 sets the outer useful diameter of the laser pulse beam 66. In turn the zoom determines the size of the beam at the aperture location and therefore the amount of light that is transmitted. The amount of transmitted light is bounded both high and low. The upper is bounded by the requirement to achieve the highest numerical aperture achievable in the eye. High NA promotes low threshold energies and greater safety margin for untargeted tissue. The lower is bound by the requirement for high optical throughput. Too much transmission loss in the system shortens the lifetime of the system as the laser output and system degrades over time. Additionally, consistency in the transmission through this aperture promotes stability in determining optimum settings (and sharing of) for each procedure. Typically to achieve optimal performance the transmission through this aperture as set to be between 88% to 92%.

After exiting the aperture 72, the laser pulse beam 66 proceeds through two output pickoffs 74. Each output pickoff 74 can include a partially reflecting mirror to divert a portion of each laser pulse to a respective output monitor 76. Two output pickoffs 74 (e.g., a primary and a secondary) and respective primary and secondary output monitors 76 are used to provide redundancy in case of malfunction of the primary output monitor 76.

After exiting the output pickoffs 74, the laser pulse beam 66 proceeds through a system-controlled shutter 78. The system-controlled shutter 78 ensures on/off control of the laser pulse beam 66 for procedural and safety reasons. The two output pickoffs precede the shutter allowing for monitoring of the beam power, energy, and repetition rate as a pre-requisite for opening the shutter.

After exiting the system-controlled shutter 78, the optical beam proceeds through an optics relay telescope 80. The optics relay telescope 80 propagates the laser pulse beam 66 over a distance while accommodating positional and/or directional variability of the laser pulse beam 66, thereby providing increased tolerance for component variation. As an example, the optical relay can be a keplerian afocal telescope that relays an image of the aperture position to a conjugate position near to the xy galvo mirror positions. In this way, the position of the beam at the XY galvo location is invariant to changes in the beams angle at the aperture position. Similarly the shutter does not have to precede the relay and may follow after or be included within the relay.

After exiting the optics relay telescope 80, the laser pulse beam 66 is transmitted to the shared optics 50, which propagates the laser pulse beam 66 to the patient interface 52. The laser pulse beam 66 is incident upon a beam combiner 82, which reflects the laser pulse beam 66 while transmitting optical beams from the ranging subsystem 46 and the alignment guidance subsystem 48.

Following the beam combiner 82, the laser pulse beam 66 continues through a Z-telescope 84, which is operable to scan focus position of the laser pulse beam 66 in the patient's eye 43 along the Z axis. For example, the Z-telescope 84 can include a Galilean telescope with two lens groups (each lens group includes one or more lenses). One of the lens groups moves along the Z axis about the collimation position of the Z-telescope 84. In this way, the focus position of the spot in the patient's eye 43 moves along the Z axis. In general, there is a relationship between the motion of lens group and the motion of the focus point. For example, the Z-telescope can have an approximate 2× beam expansion ratio and close to a 1:1 relationship of the movement of the lens group to the movement of the focus point. The exact relationship between the motion of the lens and the motion of the focus in the z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as z-scan device for scanning the focus point of the laser-pulse beam 66 in the patient's eye 43. The Z-telescope 84 can be controlled automatically and dynamically by the control electronics 54 and selected to be independent or to interplay with the X and Y scan devices described next.

After passing through the Z-telescope 84, the laser pulse beam 66 is incident upon an X-scan device 86, which is operable to scan the laser pulse beam 66 in the X direction, which is dominantly transverse to the Z axis and transverse to the direction of propagation of the laser pulse beam 66. The X-scan device 86 is controlled by the control electronics 54, and can include suitable components, such as a motor, galvanometer, or any other well known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 86, the laser pulse beam 66 is incident upon a Y-scan device 88, which is operable to scan the laser pulse beam 66 in the Y direction, which is dominantly transverse to the X and Z axes. The Y-scan device 88 is controlled by the control electronics 54, and can include suitable components, such as a motor, galvanometer, or any other well known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-Scan device 86 and the Y-Scan device 88 can be provided by an XY-scan device configured to scan the laser pulse beam 66 in two dimensions transverse to the Z axis and the propagation direction of the laser pulse beam 66. The X-scan and Y-scan devices 86, 88 change the resulting direction of the laser pulse beam 66, causing lateral displacements of UF focus point located in the patient's eye 43.

After being directed by the Y-scan device 88, the laser pulse beam 66 passes through a beam combiner 90. The beam combiner 90 is configured to transmit the laser pulse beam 66 while reflecting optical beams to and from a video subsystem 92 of the alignment guidance subsystem 48.

After passing through the beam combiner 90, the laser pulse beam 66 passes through an objective lens assembly 94. The objective lens assembly 94 can include one or more lenses. In many embodiments, the objective lens assembly 94 includes multiple lenses. The complexity of the objective lens assembly 94 may be driven by the scan field size, the focused spot size, the degree of telecentricity, the available working distance on both the proximal and distal sides of objective lens assembly 94, as well as the amount of aberration control.

After passing through the objective lens assembly 94, the laser pulse beam 66 passes through the patient interface 52. As described above, in many embodiments, the patient interface 52 includes a patient interface lens 96 having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface of the patient interface lens 96 and the patient's cornea and forms part of an optical transmission path between the shared optics 50 and the patient's eye 43.

The shared optics 50 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern (using the aim beam 108 described below) need not be identical to the treatment pattern (using the laser pulse beam 66), but can optionally be used to designate the boundaries of the treatment pattern to provide verification that the laser pulse beam 66 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, the ranging beam 102 need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also the optics shared by the alignment guidance: video subsystem does not have to be identical to those shared by the treatment beam. The positioning and character of the laser pulse beam 66 and/or the scan pattern the laser pulse beam 66 forms on the eye 43 may be further controlled by use of an input device such as a joystick, or any other appropriate user input device (e.g., control panel/GUI 56) to position the patient and/or the optical system.

The control electronics 54 can be configured to target the targeted structures in the eye 43 and ensure that the laser pulse beam 66 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally the ranging subsystem such as an OCT can be used to detect features or aspects involved with the patient interface. Features can include fiducials placed on the docking structures and optical structures of the disposable lens such as the location of the anterior and posterior surfaces.

In the embodiment of FIG. 3, the ranging subsystem 46 includes an OCT imaging device. Additionally or alternatively, imaging modalities other than OCT imaging can be used. An OCT scan of the eye can be used to measure the spatial disposition (e.g., three dimensional coordinates such as X, Y, and Z of points on boundaries) of structures of interest in the patient's eye 43. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 54 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others. Additionally the ranging subsystem such as an OCT can be used to detect features or aspects involved with the patient interface. Features can include fiducials placed on the docking structures and optical structures of the disposable lens such as the location of the anterior and posterior surfaces.

The ranging subsystem 46 in FIG. 3 includes an OCT light source and detection device 98. The OCT light source and detection device 98 includes a light source that generates and emits an OCT source beam with a suitable broad spectrum. For example, in many embodiments, the OCT light source and detection device 98 generates and emits the OCT source beam with a broad spectrum from 810 nm to 850 nm wavelength. The generated and emitted light is coupled to the device 98 by a single mode fiber optic connection.

The OCT source beam emitted from the OCT light source and detection device 98 is passed through a pickoff/combiner assembly 100, which divides the OCT source beam into a sample beam 102 and a reference portion 104. A significant portion of the sample beam 102 is transmitted through the shared optics 50. A relative small portion of the sample beam is reflected from the patient interface 52 and/or the patient's eye 43 and travels back through the shared optics 50, back through the pickoff/combiner assembly 100 and into the OCT light source and detection device 98. The reference portion 104 is transmitted along a reference path 106 having an adjustable path length. The reference path 106 is configured to receive the reference portion 104 from the pickoff/combiner assembly 100, propagate the reference portion 104 over an adjustable path length, and then return the reference portion 106 back to the pickoff/combiner assembly 100, which then directs the returned reference portion 104 back to the OCT light source and detection device 98. The OCT light source and detection device 98 then directs the returning small portion of the sample beam 102 and the returning reference portion 104 into a detection assembly, which employs a time domain detection technique, a frequency detection technique, or a single point detection technique. For example, a frequency domain technique can be used with an OCT wavelength of 830 nm and bandwidth of 100 nm.

Once combined with the UF laser pulse beam 66 subsequent to the beam combiner 82, the OCT sample beam 102 follows a shared path with the UF laser pulse beam 66 through the shared optics 50 and the patient interface 52. In this way, the OCT sample beam 102 is generally indicative of the location of the UF laser pulse beam 66. Similar to the UF laser beam, the OCT sample beam 102 passes through the Z-telescope 84, is redirected by the X-scan device 86 and by the Y-scan device 88, passes through the objective lens assembly 94 and the patient interface 52, and on into the eye 43. Reflections and scatter off of structures within the eye provide return beams that retrace back through the patient interface 52, back through the shared optics 50, back through the pickoff/combiner assembly 100, and back into the OCT light source and detection device 98. The returning back reflections of the sample beam 102 are combined with the returning reference portion 104 and directed into the detector portion of the OCT light source and detection device 98, which generates OCT signals in response to the combined returning beams. The generated OCT signals that are in turn interpreted by the control electronics to determine the spatial disposition of the structures of interest in the patient's eye 43. The generated OCT signals can also be interpreted by the control electronics to measure the position and orientation of the patient interface 52, as well as to determine whether there is liquid disposed between the posterior surface of the patient interface lens 96 and the patient's eye 43.

The OCT light source and detection device 98 works on the principle of measuring differences in optical path length between the reference path 106 and the sample path. Therefore, different settings of the Z-telescope 84 to change the focus of the UF laser beam do not impact the length of the sample path for an axially stationary surface in the eye of patient interface volume because the optical path length does not change as a function of different settings of the Z-telescope 84. The ranging subsystem 46 has an inherent Z range that is related to the light source and detection scheme, and in the case of frequency domain detection the Z range is specifically related to the spectrometer, the wavelength, the bandwidth, and the length of the reference path 106. In the case of ranging subsystem 46 used in FIG. 3, the Z range is approximately 4-5 mm in an aqueous environment. Extending this range to at least 20-25 mm involves the adjustment of the path length of the reference path via a stage ZED, 106 within ranging subsystem 46. Passing the OCT sample beam 102 through the Z-telescope 84, while not impacting the sample path length, allows for optimization of the OCT signal strength. This is accomplished by focusing the OCT sample beam 102 onto the targeted structure. The focused beam both increases the return reflected or scattered signal that can be transmitted through the single mode fiber and increases the spatial resolution due to the reduced extent of the focused beam. The changing of the focus of the sample OCT beam can be accomplished independently of changing the path length of the reference path 106.

Because of the fundamental differences in how the sample beam 102 (e.g., 810 nm to 850 nm wavelengths) and the UF laser pulse beam 66 (e.g., 1020 nm to 1050 nm wavelengths) propagate through the shared optics 50 and the patient interface 52 due to influences such as immersion index, refraction, and aberration, both chromatic and monochromatic, care must be taken in analyzing the OCT signal with respect to the UF laser pulse beam 66 focal location. A calibration or registration procedure as a function of X, Y, and Z can be conducted in order to match the OCT signal information to the UF laser pulse beam focus location and also to the relative to absolute dimensional quantities.

There are many suitable possibilities for the configuration of the OCT interferometer. For example, alternative suitable configurations include time and frequency domain approaches, single and dual beam methods, swept source, etc, are described in U.S. Pat. Nos. 5,748,898; 5,748,352; 5,459,570; 6,111,645; and 6,053,613.

The system 2 can be set to locate the anterior and posterior surfaces of the lens capsule and cornea and ensure that the UF laser pulse beam 66 will be focused on the lens capsule and cornea at all points of the desired opening. Imaging modalities and techniques described herein, such as for example, Optical Coherence Tomography (OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber, and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Observation of an aim beam can also be used to assist in positioning the focus point of the UF laser pulse beam 66. Additionally, an aim beam visible to the unaided eye in lieu of the infrared OCT sample beam 102 and the UF laser pulse beam 66 can be helpful with alignment provided the aim beam accurately represents the infrared beam parameters. The alignment guidance subsystem 48 is included in the assembly 62 shown in FIG. 3. An aim beam 108 is generated by an aim beam light source 110, such as a laser diode in the 630-650 nm range.

Once the aim beam light source 110 generates the aim beam 108, the aim beam 108 is transmitted along an aim path 112 to the shared optics 50, where it is redirected by a beam combiner 114. After being redirected by the beam combiner 114, the aim beam 108 follows a shared path with the UF laser pulse beam 66 through the shared optics 50 and the patient interface 52. In this way, the aim beam 108 is indicative of the location of the UF laser pulse beam 66. The aim beam 108 passes through the Z-telescope 84, is redirected by the X-scan device 86 and by the Y-scan device 88, passes through the beam combiner 90, passes through the objective lens assembly 94 and the patient interface 52, and on into the patient's eye 43.

The video subsystem 92 is operable to obtain images of the patient interface and the patient's eye. The video subsystem 92 includes a camera 116, an illumination light source 118, and a beam combiner 120. The video subsystem 92 gathers images that can be used by the control electronics 54 for providing pattern centering about or within a predefined structure. The illumination light source 118 can be generally broadband and incoherent. For example, the light source 118 can include multiple LEDs. The wavelength of the illumination light source 118 is preferably in the range of 700 nm to 750 nm, but can be anything that is accommodated by the beam combiner 90, which combines the light from the illumination light source 118 with the beam path for the UF laser pulse beam 66, the OCT sample beam 102, and the aim beam 108 (beam combiner 90 reflects the video wavelengths while transmitting the OCT and UF wavelengths). The beam combiner 90 may partially transmit the aim beam 108 wavelength so that the aim beam 108 can be visible to the camera 116. An optional polarization element can be disposed in front of the illumination light source 118 and used to optimize signal. The optional polarization element can be, for example, a linear polarizer, a quarter wave plate, a half-wave plate or any combination. An additional optional analyzer can be placed in front of the camera. The polarizer analyzer combination can be crossed linear polarizers thereby eliminating specular reflections from unwanted surfaces such as the objective lens surfaces while allowing passage of scattered light from targeted surfaces such as the intended structures of the eye. The illumination may also be in a dark-field configuration such that the illumination sources are directed to the independent surfaces outside the capture numerical aperture of the image portion of the video system. Alternatively the illumination may also be in a bright field configuration. In both the dark and bright field configurations, the illumination light source maybe be used as a fixation beam for the patient. The illumination may also be used to illuminate the patients pupil to enhance the pupil iris boundary to facilitate iris detection and eye tracking. A false color image generated by the near infrared wavelength or a bandwidth thereof may be acceptable.

The illumination light from the illumination light source 118 is transmitted through the beam combiner 120 to the beam combiner 90. From the beam combiner 90, the illumination light is directed towards the patient's eye 43 through the objective lens assembly 94 and through the patient interface 94. The illumination light reflected and scattered off of various structures of the eye 43 and patient interface travel back through the patient interface 94, back through the objective lens assembly 94, and back to the beam combiner 90. At the beam combiner 90, the returning light is directed back to the beam combiner 120 where the returning light is redirected toward the camera 116. The beam combiner can be a cube, plate, or pellicle element. It may also be in the form of a spider mirror whereby the illumination transmits past the outer extent of the mirror while the image path reflects off the inner reflecting surface of the mirror. Alternatively, the beam combiner could be in the form of a scraper mirror where the illumination is transmitted through a hole while the image path reflects off of the mirrors reflecting surface that lies outside the hole. The camera 116 can be an suitable imaging device, for example but not limited to, any silicon based detector array of the appropriately sized format. A video lens forms an image onto the camera's detector array while optical elements provide polarization control and wavelength filtering respectively. An aperture or iris provides control of imaging NA and therefore depth of focus and depth of field and resolution. A small aperture provides the advantage of large depth of field that aids in the patient docking procedure. Alternatively, the illumination and camera paths can be switched. Furthermore, the aim light source 110 can be made to emit infrared light that would not be directly visible, but could be captured and displayed using the video subsystem 92.

Figure 4:
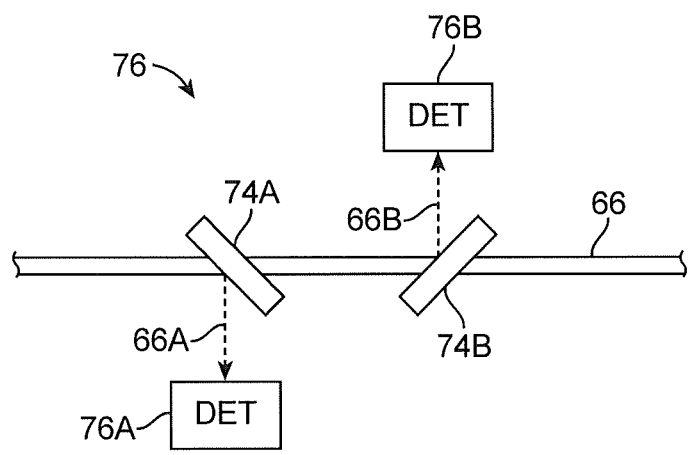
FIG. 4 shows components of the output energy monitor to measure laser beam energy, in accordance with many embodiments.

FIG. 4 shows components of an output energy monitor 76 comprising a first light energy detector 76A to measure laser beam energy and a second light energy detector 76B to measure laser beam energy. The two output pickoffs 74 may comprise a first beam splitter 74A and a second beam splitter 74B. The first beam splitter 74A directs a first portion 66A of beam 66 to first detector 76A. The second beam splitter 74B directs a second portion 66B of beam 66 to second detector 76B. In many embodiments, the first and second detectors energy detectors are coupled to the circuitry to measure the laser beam energy as described herein.

Figure 5:
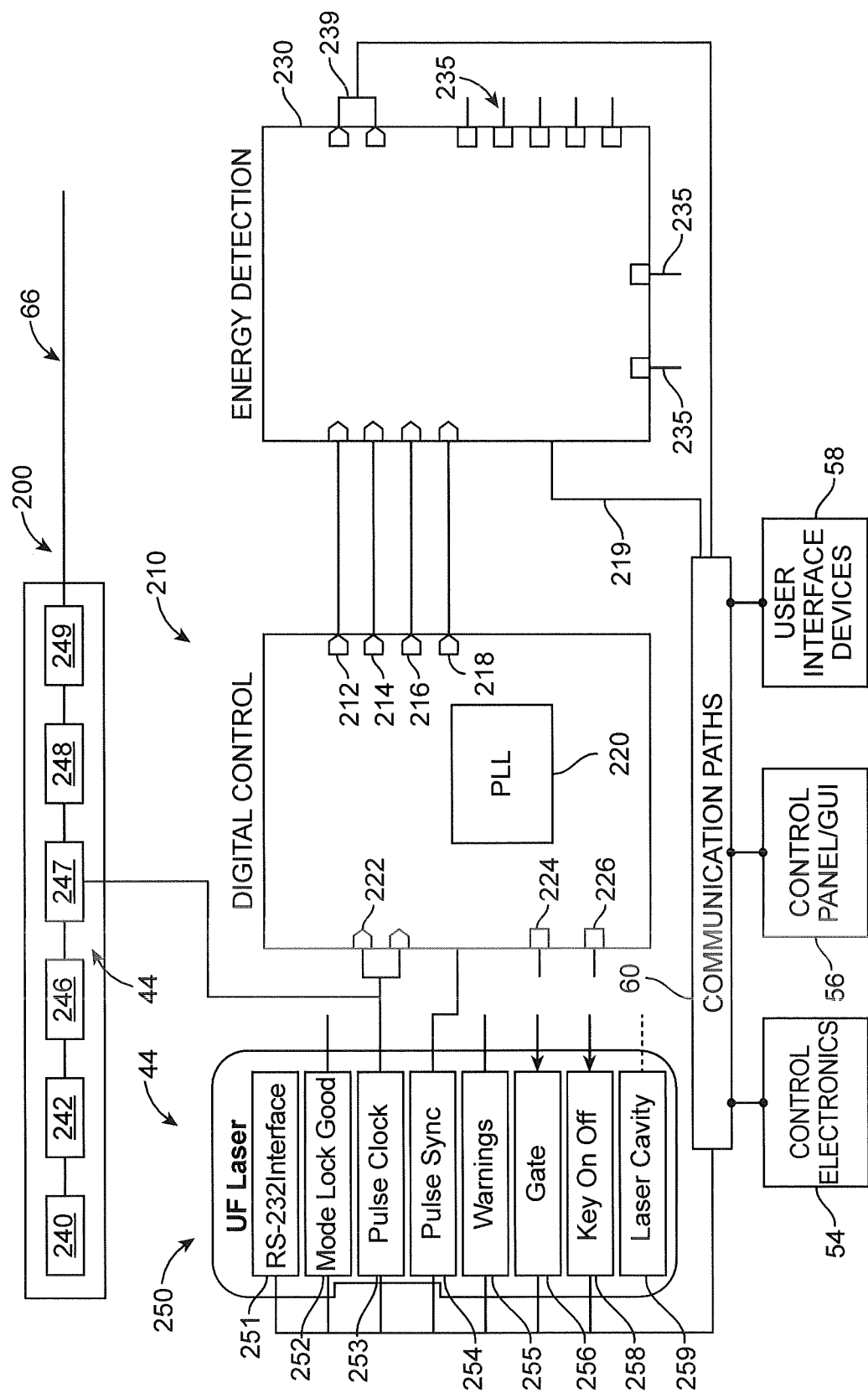
FIGS. 5 and 6 show circuitry capable of measuring each pulse of the pulsed laser beam with a plurality of integrators, in accordance with many embodiments.
Figure 6:
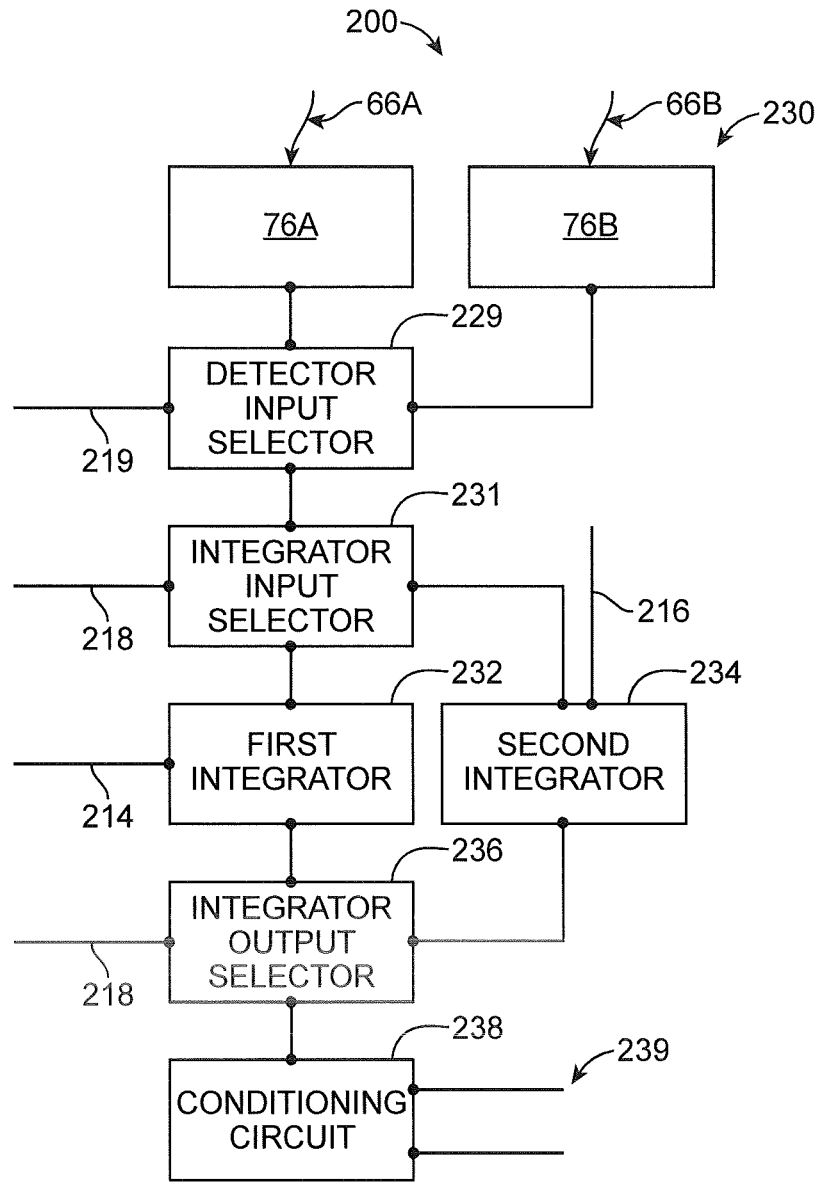

FIGS. 5 and 6 show circuitry 200 capable of measuring each pulse of the pulsed laser beam with a plurality of integrators. The circuitry 200 comprises digital control circuitry 210, energy detection circuitry 230 and interface circuitry 250 of ultrafast (hereinafter "UF") pulsed laser 44. The digital control circuitry 210 is coupled to laser interface circuitry 250 and configured to receive signals from interface circuitry 250 in order to toggle coupling of detector 76A between the first integrator 232 and the second integrator 234.

The circuitry 200 for measuring each pulse can be located along the beam path of cutting laser 44 as described herein. Alternatively or in combination, the circuitry 200 may be located further along the optical path, for example near the eye of the patient to measure each pulse of the laser beam, for example to determine transmission efficiency through the delivery system.

The interface circuitry 250 of laser 44 may comprise one of more of the following interface lines to transmit a signal: RS-232 interface 251; mode lock good 252; pulse clock 253; pulse sync 254; warnings 255; gate 256; key on/off 258; or laser cavity 259 signals.

The laser 44 may comprise one or more components of the laser system as described herein. In exemplary embodiments, laser 44 comprises a mode locked laser 240 comprising a seed laser to provide seed pulses to an optical amplifier 246, which may comprise an optical fiber amplifier such as an Erbium optical amplifier. A pulse stretcher 242 can be located between the mode locked laser 240 and the optical amplifier 246. A pulse picker 247 can be located after the optical amplifier 244. The pulse picker 247 can pick amplified pulses and transmit the picked amplified pulses to a second optical amplifier 248. The pulses amplified by the second optical amplifier can be transmitted to a pulse compressor 249. The pulsed laser beam 66 may comprise a plurality of pulses compressed with pulse compressor 249.

Although the above described configuration of the laser 44 can be used, a person of ordinary skill in the art will recognize many variations in accordance with the teachings described herein, and the arrangement of the pulse stretcher 242, the first optical amplifier 246, the pulse picker 247, the second optical amplifier 248 and the pulse compressor 249 can vary such that the beam passes through one or more of these components of laser 44 in a different order.

The laser interface 250 comprises pulse clock 253 and pulse sync 254, and one or more of the pulse clock 253 or pulse sync 254 can be coupled to the digital control circuitry 210 and energy detection circuitry 230 in order to toggle the energy detector 76A between the first integrator and the second integrator in synchronization with pulse picker 246 picking the laser beam from the mode locked laser for transmission to the detector. In many embodiments, the laser clock is coupled to the digital control circuitry 210. Alternatively or in combination, the pulse sync 253 may be coupled to the digital control circuitry 210. The digital control circuitry may comprise one or more of controller or processor circuitry as described herein. In many embodiments, digital control circuitry 210 comprises a phase locked loop to measure energy of laser 44 based on one or more of pulse clock 253 or pulse sync 254, for example. The signals of the laser interface 250 can be connected to the communication paths 60 so as to transmit the signals from the laser system to other components of system 2 as described herein, such as control electronics 54, control panel/GUI 56, and user interface device 5, for example.

The digital control circuitry 210 can be configured to output signals to energy detector circuitry based on the input signals from the laser interface 250. The digital control circuitry 210 can be configured to output one or more of a phased locked loop error signal 212, an integrator 1 reset signal 214, an integrator 2 reset signal 216 or an integrator select signal 218. The phased locked loop error signal can indicate that the pulse did not occur, or an error locking the phased locked loop on the laser pulse signals such as the pulse clock 253 and the pulse sync 254, for example. The integrator 1 reset 214 provides a digital signal to reset the first integrator as described herein. The integrator 2 reset 216 provides a digital signal to reset the second integrator as described herein. The integrator select 218 provides a digital signal to select the integrator to couple to the detector.

The control electronics 54 can be coupled to the energy detection circuitry 230 and may comprise a detector select command to identify first detector 76A or second detector 76B for energy measurement with a detector select signal 219, for example.

The energy detection circuitry 230 comprises circuitry to measure the energy from the detector 76A, and may comprise switching circuitry to switch the connections that coupled the detector 76A to the plurality of integrators comprising, the first integrator 232, and the second integrator 234. The energy detection circuitry 230 comprises an integrator input selector 231 coupled to the integrator select 218 to receive the integrator select signal in order to select the integrator to couple to detector 76A, for example. The input to the integrator input selector is coupled to the output of the detector 76A. Alternatively, the input of the integrator input selector may be coupled to an output of a detector selector 229. The first integrator 232 and the second integrator 234 are coupled to the output of integrator input selector 231. The output of the first integrator 232 and the output of the second integrator 234 are connected to an input of an integrator output selector 236. The integrator output selector 236 is coupled to the integrator select 218 to select the integrator to output. The output of the integrator output selector 236 is coupled to conditioning circuitry 238 to output the amount of light energy measured with photo detector with an output 239 of the energy detection circuitry 230. The output of the integrator output selector is coupled to the integrator decoupled from the detector to output the integrated measurement from the photo detector.

Additional signals can be provided with the circuitry as described herein. For example a transmit photo detector signal 217 can be provided to transmit the amount of measured light from output 239 to the control electronics 54. For example, the amount of light energy can be measured for each pulse selected with pulse picker 247 and transmitted to control electronics 54 for analysis and control of system 2.

The energy detection circuitry 230 can be powered in one or more of many known ways and can be powered with a plurality of voltages 235 comprising a first positive voltage, a second positive voltage, a first negative voltage, a second negative voltage, a positive reference voltage, a negative reference voltage and coupling to ground, for example.

A person of ordinary skill in the art will recognize that the plurality of integrators may comprise more than two integrators and as many integrators as helpful to measure high repetition rate laser firing as described herein and may comprise three or more integrators, or five or more detectors for example. In many embodiments, the number of integrators used in the circuit will depend upon the integration time to respond to the detector.

The energy of second detector 76B can be measured with circuitry similar to energy detection circuitry 230, for example with a redundant back up energy detection circuitry similar to energy detection circuitry 230. Alternatively, a detector input selector circuitry can be provided to couple the first detector 76A or the second detector 76B with the integrator input selector 230.

The first energy detector 76A and the second energy detector 76B may comprise substantially similar energy detectors, and may comprise one or more of many energy detectors know to measure energy of a laser beam by a person of ordinary skill in the art. In many embodiments the first energy detector 76A and the second energy detector 76B each comprise a reverse biased photo diode having similar surface areas. In the reversed bias configuration, the photo diode passes an amount of electrical current to the integrator in proportion to the amount of light energy illuminating the reverse biased diode with the laser beam pulse.

Figure 7:
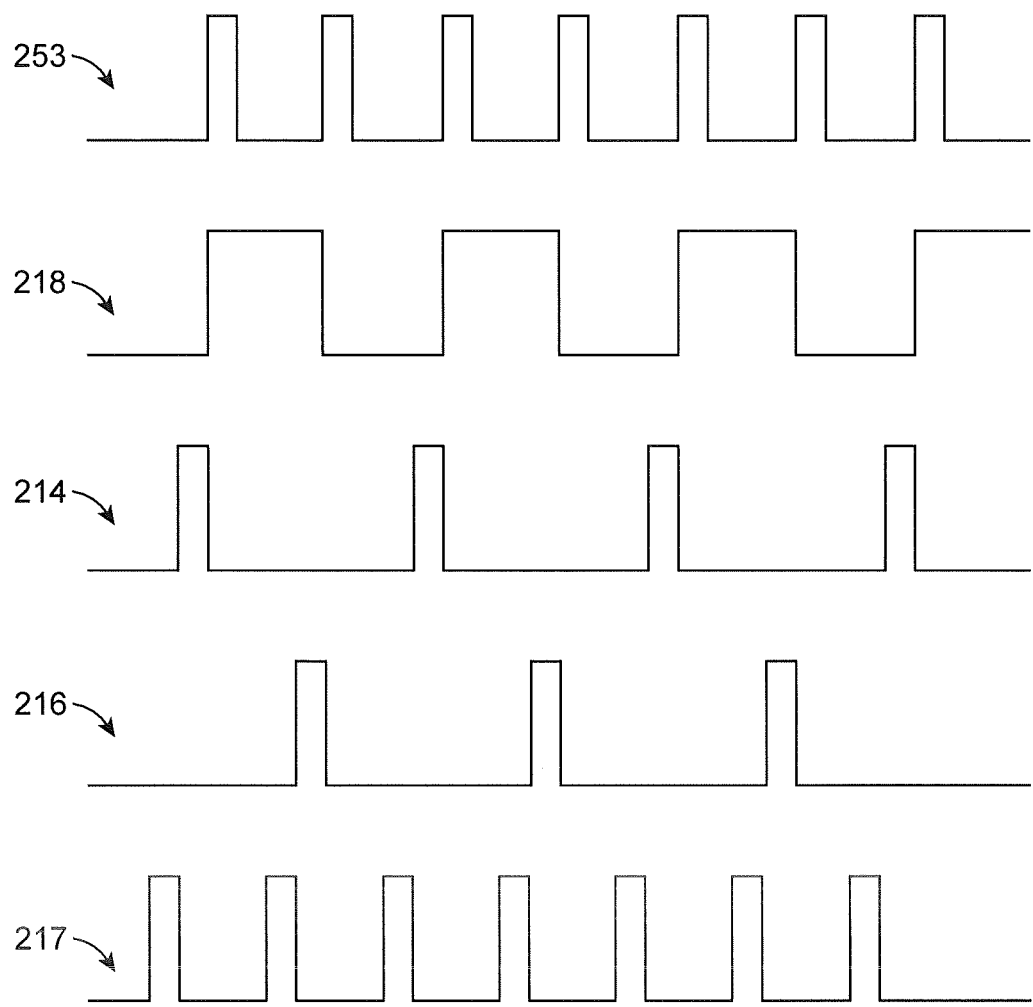
FIG. 7 shows a timing diagram of the circuitry of FIGS. 5 and 6.

FIG. 7 shows a timing diagram of the circuitry of FIGS. 5 and 6. The integrator select 218 can select the integrator that is coupled to the detector with a logic signal so that the integrator has been reset and is coupled to the detector 76A when the pulse arrives from beam 66. The first integrator reset 214 can reset the voltage of the first integrator 232 a few or tens of microseconds before the integrator input selector 230 couples the first integrator 232 to the detector 76A, for example. The second integrator reset 216 can reset the voltage of the second integrator 234 a few or tens of microseconds before the integrator input selector 230 couples the second integrator to the detector 76A, for example. The laser pulse clock 253 can be input to the digital control circuitry 210 so that the reset first or second integrator is coupled to the detector 76A when the laser fires and the integrator decoupled from the detector 76A, for example, continues to integrate when the laser pulses with the signal to pulse picker 246.

An output data signal 217 can transmit the measured amount of energy to other system components as described herein, for example control electronics 54.

FIG. 8 shows a method 300 of treating a material such as tissue, for example with eye surgery. The method 300 may use one or more of the structures as described herein, and one or more functions of the one or more structures may be used to perform the method 300 as described herein.

At a step 305, the type of treatment is determined, for example type of material, surgical procedure, location of treatment.

At a step 310, the treatment input is received from the user.

At a step 315, patient measurement data is received, for example from an OCT machine.

At a step 320, a series of pulses to cut anterior lens capsule with 3D cutting of capsule.

At a step 325, a series of pulses is determined in order to fragment cortex and nucleus with 3D cutting.

At a step 330, the first detector or the second detector is selected to measure pulses. Alternatively, both detectors can be used to measure the energy of the pulses.

At a step 335, energy is measured of each pulse of a series of calibration pulses.

At a step 340, the first integrator is reset.

At a step 345, the first integrator is coupled to the detector.

At a step 350, the first laser beam pulse is transmitted.

At a step 355, the first laser beam pulse is received with the photo detector.

At a step 360—, integration of the first pulse is initiated with the first integrator.

At a step 365, the second integrator is reset.

At a step 370, the first integrator is decoupled from the detector.

At a step 375, the first integrator is coupled to conditioning circuit with the integrator output selector.

At a step 380, the second integrator is coupled to the detector.

At a step 385, the second laser beam pulse is transmitted.

At a step 390, the second laser pulse is received with the photo detector.

At a step 395, the integration of the second pulse is initiated with second integrator.

At a step 400, the integration of first pulse is completed.

At a step 405, an amount of energy of the first pulse is transmitted to the system controller.

At a step 410, the first integrator is reset.

At a step 415—the first integrator is coupled to the detector.

At a step 420—the second integrator is decoupled from the integrator.

At a step 425—the second integrator is coupled to the conditioning circuitry with integrator output.

At a step 430, the integration of second pulse is completed with the second integrator.

At a step 435, the amount of energy of second pulse is transmitted to the system controller.

At a step 440, the above steps are repeated to measure energy of each pulse of the laser calibration At a step 445, the output of the laser beam energy per pulse is adjusted.

At a step 450, the patient is treated.

At a step 455, each pulse of the series of pulses of the patient treatment is measured.

At a step 460, an output of the laser is adjusted during treatment.

At a step 465, treatment is completed.

Although the above steps show method 300 of treating a patient in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the treatment.

One or more of the steps of the method 300 may be performed with the circuitry as described herein, for example one or more of the processor or logic circuitry such as the programmable array logic for field programmable gate array. The circuitry may be programmed to provide one or more of the steps of method 300, and the program may comprise program instructions stored on a computer readable memory or programmed steps of the logic circuitry such as the programmable array logic or the field programmable gate array, for example.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. An apparatus to treat a material with pulsed light energy, the apparatus comprising:
    a pulsed laser to generate light energy comprising a plurality of pulses to treat the material;
    a detector responsive to the light energy;
    a plurality of integrators comprising a first integrator and a second integrator coupled to the detector; and
    switching circuitry coupled to the pulsed laser, the detector and the plurality of integrators to couple the detector to the first integrator for a first time interval that includes an entire duration of a first pulse of the light energy and the second integrator for a second time interval that includes an entire duration of a second pulse of the light energy which is different from the first pulse.

2. The apparatus of claim 1, further comprising:
    an optical delivery system coupled to the pulsed laser to deliver a series of pulses to the material, wherein each pulse of the series is capable of optical breakdown when focused; and
    a controller coupled to the pulsed laser, the optical delivery system, and the first integrator and the second integrator;
    wherein the controller measures the energy of the series of pulses applied to the material from the first integrator and the second integrator and wherein the controller adjusts output energy of the pulsed laser in response to the energy measured from the first integrator and the second integrator.

3. The apparatus of claim 2, wherein the controller measures each pulse of the series of pulses with the first integrator and the second integrator and adjusts the output energy in response to the measured energy.

4. The apparatus of claim 1, wherein the pulsed laser comprises an optical switch coupled to the switching circuitry and wherein the optical switch transmits the first pulse of the light energy to the detector with the detector coupled to the first integrator and transmits the second pulse of the light energy to the detector with the detector coupled to the second integrator.

5. The apparatus of claim 4, wherein the pulsed laser comprises a mode locked laser and wherein the optical switch comprises a pulse picker coupled to the switching circuitry to pick the first pulse from a first plurality of mode locked pulses and the second pulse from a second plurality of mode locked pulses.

6. The apparatus of claim 5, wherein the pulse picker transmits the first pulse to the detector with the detector coupled to the first integrator and decoupled from the second integrator and wherein the pulse picker transmits the second pulse to the detector with the detector coupled to the second integrator and decoupled from the first integrator.

7. The apparatus of claim 5, wherein pulsed laser comprises a pulse stretcher and a pulse compressor and wherein pulse picker is located along an optical path between the pulse stretcher and the pulse compressor to pick stretched pulses transmitted to the pulse compressor.

8. The apparatus of claim 5, wherein pulsed laser comprises a first optical amplifier and a second optical amplifier and wherein the pulse picker is located between the first optical amplifier and the second optical amplifier and wherein the detector is positioned along an optical path to measure picked pulses transmitted through the second optical amplifier.

9. The apparatus of claim 1, wherein the first pulse and the second pulse comprise pulses of a series of pulses, the series of pulses having a pulse frequency, and wherein the first integrator outputs energy of each pulse of a first half of the pulses at half the pulse frequency and the second integrator outputs energy of each pulse of a second half of the pulses at half the pulse frequency.

10. The apparatus of claim 1, wherein the first integrator is configured to integrate an output of the detector over a first integration time and the second integrator is configured to integrate an output of the detector over a second integration time, and wherein the first integration time and the second integration time are each greater than an amount of time between the first pulse of the light energy and the second pulse of the light energy.

11. The apparatus of claim 1, wherein the switching circuitry is configured to receive a first light pulse with the detector electrically coupled to the first integrator and a second light pulse with the detector electrically coupled to the second integrator.

12. The apparatus of claim 11, wherein the switching circuitry decouples the first integrator from the detector and couples the second integrator to the detector after the first time interval.

13. The apparatus of claim 12, wherein the switching circuitry decouples the second integrator from the detector and couples the first integrator to the detector after the second time interval.

14. The apparatus of claim 1, wherein the light energy comprises one or more of infrared light energy, visible light energy or ultraviolet light energy.

15. The apparatus of claim 1, wherein the detector comprises a plurality of detectors and wherein the plurality of detectors is coupled to the first integrator for the first time interval and the second integrator for the second time interval.

16. The apparatus of claim 1, further comprising a processor, wherein the material comprises tissue of an eye and wherein the processor is coupled to the first integrator and the second integrator to measure the first pulse and the second pulse transmitted into the tissue of the eye to treat the eye.

17. The apparatus of claim 16, wherein the eye comprises a cornea and a lens and wherein the pulses of the light energy are focused into one or more of the cornea or the lens to treat the one or more of the cornea or the lens.

18. The apparatus of claim 1, further comprising a second detector and wherein the switching circuitry is configured to switch coupling of the first integrator and the second integrator to the second detector in order to measure the first pulse with the second detector coupled to the first integrator and the second pulse with the second detector coupled to the second integrator.

19. The apparatus of claim 1, wherein the switching circuitry comprises one or more of a phase locked loop or a flip flop to toggle the coupling of the detector back and forth between the first integrator and the second integrator and wherein the one or more of the phase locked loop or the flip flop is coupled to a laser clock to synchronize switching between the first integrator and the second integrator between the pulses of the laser beam light energy.

20. An apparatus, comprising:
a pulsed laser configured to generate light energy comprising a plurality of pulses which are capable of optical breakdown of a material in an eye;
a detector having an input configured to receive at least a portion of the light energy, and further having an output, wherein the detector is configured to provide an electrical detection signal to the output in response to the received portion of the light energy;
a first integrator and a second integrator, each of the first and second integrators having a corresponding input and a corresponding output;
a conditioning circuit having an input;
integrator input switching circuitry coupled to the output of the detector and further coupled to the inputs of the plurality of integrators, wherein the integrator input switching circuitry is configured to couple the electrical detection signal to the input of the first integrator for a first time interval that includes an entire duration of a first pulse of the light energy and to couple the electrical detection signal to the input of the second integrator for a second time interval that includes an entire duration of a second pulse of the light energy; and
integrator output switching circuitry coupled to the outputs of the integrators and further coupled to the input of the conditioning circuit, wherein the integrator output switching circuitry is configured to connect the output of the first integrator to the input of the conditioning circuit for the first time interval and to connect the output of the second integrator to the input of the conditioning circuit for the second time interval.

21. The apparatus of claim 20, further comprising one or more of a phase locked loop and a flip flop configured to supply a switching signal to the integrator input switching circuitry to toggle the coupling of the electrical detection signal back and forth between the input of first integrator and the input of the second integrator, and wherein the one or more of the phase locked loop and the flip flop is coupled to a laser clock of the pulsed laser to synchronize the switching signal to the first and second pulses of the of the light energy.

22. The apparatus of claim 20,
wherein the pulsed laser comprises a mode locked laser, and includes an optical switch comprising a pulse picker configured to pick the first pulse from a first plurality of mode locked pulses and the second pulse from a second plurality of mode locked pulses; and
wherein the optical switch is configured to transmit the first pulse to the input of the detector while the output of the detector is coupled to the input of the first integrator and decoupled from the input to the second integrator, and to transmit the second pulse to the input of the detector while the output of the detector is coupled to input of the second integrator and decoupled from the input to the first integrator.

23. The apparatus of claim 20, wherein the first integrator is configured to intergrade over a first integration time and the second integrator is configured to integrate over a second integration time, and wherein the first integration time and the second integration time are each greater than an amount of time between the first pulse of the light energy and the second pulse of the light energy.

* * * * *